United States Patent [19]

Hoffman et al.

[11] Patent Number: 4,999,340

[45] Date of Patent: Mar. 12, 1991

[54] REHYDRATABLE AGAROSE GELS

[75] Inventors: Wayne L. Hoffman; Adrien A. Jump, both of Dallas, Tex.

[73] Assignee: Board of Regents, The University of Texas System, Austin, Tex.

[21] Appl. No.: 229,071

[22] Filed: Aug. 4, 1988

[51] Int. Cl.$^5$ .......................... A61K 31/00; C08J 3/00
[52] U.S. Cl. ........................................ 514/23; 514/53; 514/54; 514/57; 514/944; 524/55; 435/7.1; 436/514; 436/515; 436/516
[58] Field of Search ........................ 514/23, 53, 54, 57, 514/944; 524/55; 435/7; 436/514, 515, 516

[56] References Cited

U.S. PATENT DOCUMENTS

| | | | |
|---|---|---|---|
| 3,527,712 | 9/1970 | Renn et al. | 252/316 |
| 3,578,604 | 5/1971 | Uriel | 252/316 |
| 3,875,044 | 4/1975 | Renn et al. | 204/299 |
| 3,878,100 | 4/1975 | Bixler | 210/198 |
| 3,922,432 | 11/1975 | Renn | 428/327 |
| 4,048,377 | 9/1977 | Boschetti et al. | 428/474 |
| 4,189,370 | 2/1980 | Boschetti | 204/299 |
| 4,192,784 | 3/1980 | Brown et al. | 260/8 |
| 4,290,911 | 9/1981 | Cook et al. | 252/316 |
| 4,319,976 | 3/1982 | Gurske | 204/180 |
| 4,668,359 | 5/1987 | Postle et al. | 204/182.7 |
| 4,737,533 | 4/1988 | Charmot et al. | 524/22 |

OTHER PUBLICATIONS

Horowitz et al., "Electrophoresis of Proteins and Nucleic Acids on Acrylamide-Agarose Gels Lacking Covalent Cross-Linkings", Anal. Biochem., vol. 143 (1984) 333–340.

Bode, "The Use of Liquid Polyacrylamide in Electrophoresis I. Mixed Gels Composed of Agar-Agar and Liquid Polyacrylamide", Anal. Biochem., vol. 83 (1977) 204–210.

Johansson et al., "Electrophoresis, Cross Immunoelectrophoresis, and Isoelectric Focusing in Agarose Gels With Reduced Electroendosmotic Flow", Anal. Biochem., vol. 59 (1974) 200–213.

Bode, "The Use of Liquid Polyacrylamide in Electrophoresis II. Relationship Between Viscosity and Molec-
(List continued on next page.)

Primary Examiner—Ronald W. Griffin
Assistant Examiner—Everett White
Attorney, Agent, or Firm—Arnold, White & Durkee

[57] ABSTRACT

The present invention involves a method for separating biological molecules by subjection of said molecules to a separation system in a gel medium. The method most particularly involves the use of a gel slab suitable for such separations which is readily equilibrated with an appropriate solvent for the chosen separation system. An important aspect of the present invention involves the initial preparation of a gel slab comprising between about 0.5% and about 2.0% agarose and between about 1% and about 3.0% linear water-soluble and substantially nonionic polyacrylamide. A preferred gel slab of the present invention contains between about 1% and 3% agarose and about 3% linear, water-soluble, substantially nonionic polyacrylamide. The gel slabs of the present invention are preferably between about 1 mm and 0.5 mm in thickness.

Said aged gel slab is then dried to produce a gel precursor sheet. A preferred drying procedure is to subject the gel slab to a stream of warm air to maintain a preferable gel surface temperature of about 45°–50° C., a 0.5 mm gel slab taking about 6–8 min to dry under these conditions. The dried gel precursor sheet, preferably maintained in a dried state for less than about 24 hr, is immersed for at least about 30 min, preferably at about 20° C., in an aqueous separation solvent compatible with the separation system to be utilized. Aqueous separation solvents usable for gel rehydration include those comprising one or more of detergents (preferably nonionic), urea (up to about 10M), ampholytes and pH buffers, for example, depending upon the particular separation system to be used for separation of the biological molecules. Usable separation systems include electrophoresis, immunodiffusion and isoelectric focusing, for example.

36 Claims, 3 Drawing Sheets

OTHER PUBLICATIONS ular Sieving", Anal. Biochem., vol. 83 (1977) 364-371.

Andrews, "Electrophoresis: Theory, Techniques, and Biochemical and Clinical Applications", Oxford Press, Cambridge (1986) 8.

Dirnhuber et al., "The Isomeric Transformation of Urea Into Ammonium Cyanate in Aqueous Solutions", Biochem. J., vol. 42 (1948) 628-632.

Stark et al., "Reactions of the Cyanate Present in Aqueous Urea With Amino Acids and Proteins", J. Biol. Chem., vol. 235 (1960) 3177-3181.

Ui, "Isoelectric Points and Conformation of Proteins I. Effective Urea on the Behavior of Some Proteins and Isoelectric Focusing", Biochim., Biophys. Acta, vol. 229 (1971) 567-581.

Silmey et al., "In Vitro Synthesis of Immunoglobulin by Rheumatoid Synovial Membrane", J. Clin. Invest., vol. 47 (1968) 624-632.

David, "Solid State Lactoperoxidiase: A Highly Stable Enzyme for Simple, Gentle Iodination of Proteins", Biochem. Biophys. Res. Commun., vol. 48 (1972) 464-471.

Hoffman et al., "Rapid Blotting of IgG to Nitrocellulose With Minimal IgM Contamination", J. Immunol. Meth., vol. 76 (1985) 263-271.

Allen et al., "Gel Electrophoresis and Isoelectric Focusing of Proteins", Walter de Gruyter, New York (1984) 84.

"The Agarose Monograph," FMC Corporation, Rockland, Maine (1982).

Olsson, et al., "Isoelectric Focusing in Agarose under Denaturing Conditions", J. Chromotography, vol. 215 (1981) 373-378.

"Methodology for Agarose Isoelectric Focusing, Immunofixation, and Related Techniques", (1982) FMC Corporation, Rockland, Maine.

Ghetie, et al., "Drying of Agarose Gel Beads", Experientia, vol. 27 (1971) 1384-1385.

Porath et al., "Agar Derivatives for Chromatography Electrophoresis and Gel Bound Enzymes", J. Chromotography, vol. 60 (1971) 167-177.

Andrews, "Electrophoresis on Agarose and Composite Polyacrylamide-Agarose Gels", Electrophoresis, Clarendon Press (1986) 148-177.

Hoffman et al. (1989), Electrophoresis, 10:741-747.

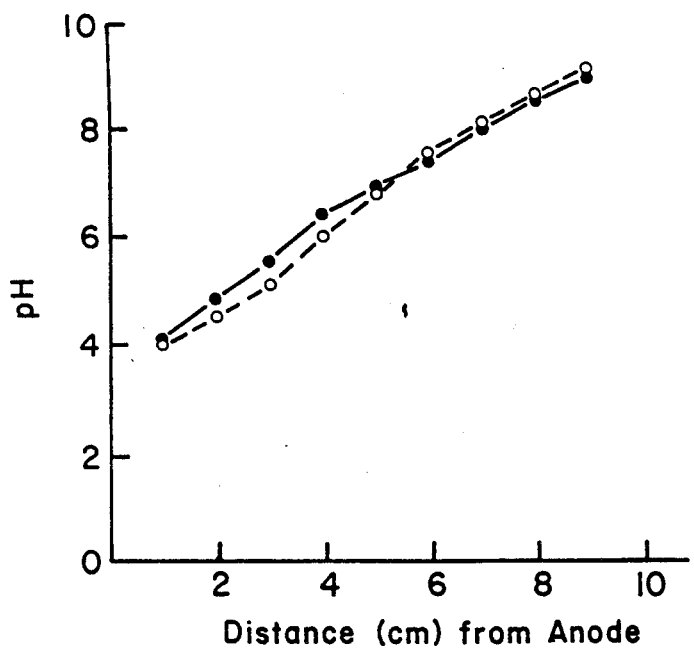
FIG. 3
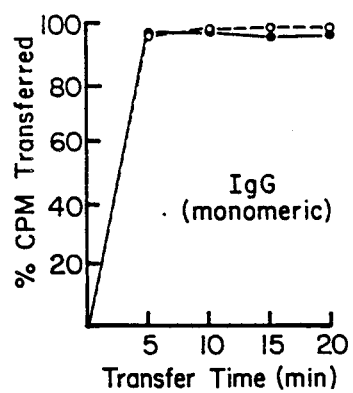 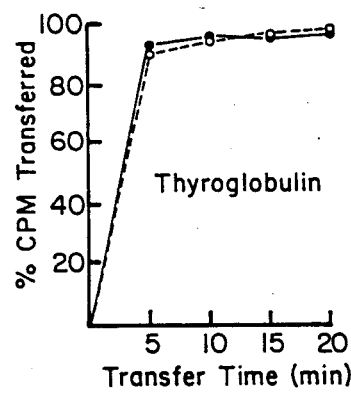 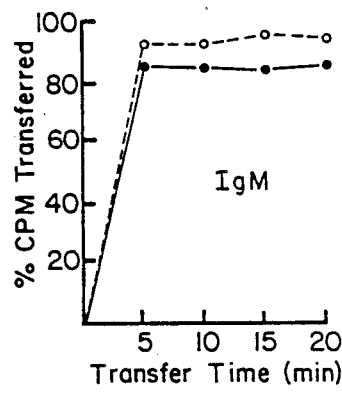
FIG. 4A  FIG. 4B  FIG. 4C

REHYDRATABLE AGAROSE GELS

BACKGROUND OF THE INVENTION

The use of an agarose gel slab which may be dried and rehydrated in an aqueous separation solvent. The rehydrated gel slab has a porosity substantially similar to that of the initially produced gel slab and is in a state of equilibration with the separation solvent and ready for use in various systems such as those for separation of biological molecules.

Agarose is a purified linear galactan hydrocolloid isolated from agar or recovered directly from agar-bearing marine algae (The Agarose Monograph (1982) FMC Corporation, Rockland, Maine). Although agarose was initially thought to be the neutral agarobiose fraction of agar, it is known to sometimes contain charged groups such as sulfate ester, ketal pyruvate, and carboxyl groups (The Agarose Monograph (1982) FMC Corporation, Rockland, Maine). The hydrated counter-ions associated with these anionic residues are responsible for the electroendosmosis observed in immunoelectrophoresis, but these charged groups can be removed or blocked to permit the use of agarose in isoelectric focusing.

Agarose is a successful anticonvection medium because it exhibits high gel strength at low concentrations. This gel strength is the result of a three-dimensional gel network based on hydrogen bonding and hydrophobic interaction. Agarose gels are used in a variety of applications and forms a macroporous, nonrestrictive matrix which allows rapid diffusion of high molecular weight macro-molecules. A large pore size, shorter run times, and lack of toxicity are the major advantages of choosing agarose over polyacrylamide for the analysis of macro-molecules. If compounds such as urea that disrupt hydrogen bond formation are present during the casting and formation of the gel, gel strength will be decreased (The Agarose Monograph (1982) FMC Corporation, Rockland, Me.) or the gel may not even form. Previously, these compounds could only be incorporated into preformed agarose gels by extended dialysis, which was not only time consuming, but was expensive with compounds such as the ampholytes necessary for isoelectric focusing.

Although it has been reported that agarose gels can be formed in the presence of 8 M urea (Olsson, I., and Laas, T. (1981) J. Chromatography 215, 373–378), these gels had a significantly lower gel strength than normal gels and could not be readily blotted with nitrocellulose for transfer of separated molecules. In addition, since these gels must cure overnight at 21° C., a significant amount of cyanate forms in the gel (Dirnhuber, P., and Schutz, F. (1948) Biochem. J., 42:628–632), which should be removed before the analysis of proteins.

The low gel strength associated with gels formed in the presence of a high urea concentration has been postulated to be related to a double helix structure of agarose which is stabilized by hydrogen bonding and hydrophobic interactions ((The Agarose Monograph (1982) FMC Corporation, Rockland, Maine). Compounds such as urea that disrupt hydrogen bonding tend to disrupt the agarose structure. In contrast, the structure of polyacrylamide is based on covalent bonding, and reagents that disrupt hydrogen bonding are compatible with the polyacrylamide gel matrix. However, the generally smaller pore size in polyacrylamide gel as compared to agarose gel, detracts from its use with large biological molecules.

In the processes of the present invention, over 4 M and up to 10 M urea may be absorbed directly into the dried agarose gel in 30 minutes. This method of rehydration and equilibration does not cause a noticeable decrease in gel strength and minimizes final cyanate concentrations. In addition, many other substances that would normally be inactivated or modified by the high temperatures preceding gelation of the agarose can be rapidly incorporated directly into the rehydratable agarose gels at 4° C. The rehydratable agarose gels can be used with any procedure employing a slab or film of agarose, including isoelectric focusing, immunoelectrophoresis and Ouchterlony immunodiffusion analysis.

Rehydratable agarose gels have previously been described, for example in Renn et al., (1970) U.S. Pat. No. 3,527,712 and Boschetti et al., (1977) U.S. Pat. No. 4,048,377. In these patents, either hydrocolloids or linear polyacrylamides (LPA) were incorporated into the agarose gels during gel formation. These compounds allowed the gels to be dehydrated and stored in a dry state. Unfortunately, the size, characteristics, and amount of the hydrocolloids and LPA used in these two patents necessitated their removal after rehydration of the agarose gels. Therefore, although the agarose gels could be rehydrated from a dry state, the subsequently required water dialysis to remove the hydrocolloids or LPA from the gels resulted in gels that still had to be dialyzed for equilibration with the reagents of choice. As a result, these rehydratable gels offered no advantage over regular gels for the rapid incorporation of 8 M urea or other reagents, into the gel matrix.

A dried rehydratable film containing agarose and linear acrylamide or methacrylamide was described in U.S. Pat. No. 4,048,377. This reference refers to a gel comprising, at most, 5% agarose and 3 to 6% linear polymer such as polyacrylamide. This gel was dried and stored for periods of time up to 8 months at 4° C. The dried gel film could be rehydrated in aqueous buffers for use in separation procedures. At this time of dried gel rehydration, this reference indicated that the linear polymer, upon the several hours of rehydration, was removed from the gel. The maintenance of gel porosity was not addressed in this reference since it was assumed that all linear polymer was removed to recreate the original gel. The present invention involves a unique methodology procedure for rapidly preparing an equilibrated gel with substantially the original porosity.

U.S. Pat. No. 3,922,432, issued to Rann, describes a thin layer gel medium for use in diffusion or affinity separation procedures. A particulate material, which may be of various substances such as polyacrylamide, carbohydrates or other water-sorptive matter, was attached to a backing sheet and could be hydrated by immersion in water and then utilized for separative purposes.

U.S. Pat. No. 3,878,100, issued to Bixler, describes a thin layer separation medium for use in molecular diffusion or other separation procedures. A thin slab comprising substances such as agarose, sodium alginate and polyethylene glycol may be prepared, dried and then rehydrated for use.

U.S. Pat. No. 3,578,604, issued to Ureal describes a gel comprising agarose and 3 to 7% cross-linked polyacrylamide. The resultant gels, in one example, were cast, washed and dehydrated in a 37° C. oven for 16 to 24 hours. The dehydrated gels were rehydrated by immersion in an aqueous bath for 8 to 16 hours.

U.S. Pat. No. 3,527,712, issued to Renn, describes gels comprising agarose and macro-molecular hydrocolloids present at a concentration in the gel between about 0.1% and about 1.0%. The gel is converted into particles, dried and then rehydrated for usage. The agarose-hydrocolloid mixture may also be formed as a thin film which may be dried and subsequently rehydrated and having the hydrocolloid removed by soaking in water.

U.S. Pat. No. 3,875,044, issued to Renn et al., describes a three layer bonded assembly including a hydratable gel material surrounding by water impervious layers.

U.S. Pat. No. 4,290,911, issued to Cook et al., describes a finely divided solid blend purified agarose and a nonionic gum which is a suitable medium for separation techniques such as isoelectric focusing.

U.S. Pat. No. 4,319,976, issued to Gurske, describes an electrophoretic gel comprising polysaccharide such as agarose and an acid polysaccharide comprising carboxyl groups.

Andrews (page 148-153, 1986) ELECTROPHORESIS, Oxford Press) describes composite polyacrylamide-agarose gels for use in the separation of biological molecules.

Horowitz et al. (Anal. Biochem., 143:333-340 (1984)) describe the electrophoresis of proteins and nucleic acids on acrylamide-agarose gels without covalent cross-linking. No particular advantages of this system appear to be outstanding, according to this reference.

Bode (Anal. Biochem., 83:204-210 (1977)) describes the use of mixed gels comprising agar-agar and liquid polyacrylamide and studies their molecular sieving properties.

Johansson et al. (Anal. Biochem., 59:200-213 (1974)) describe a method for isoelectric focusing of proteins in gels made from a mixture of purified agarose and non-cross linked polyacrylamide. It was found in this reference that polyacrylamide reduced the endoosmotic effects of agarose and sharpened protein bands obtained by separations on the gel.

Bode (Anal. Biochem., 83:364-371 (1977)) describes molecular sieving effects as influenced by the length of single polymer chains, more particularly linear polyacrylamide.

Abbreviations used herein include IEF, isoelectric focusing; LPA, linear polyacrylamide; NFDM, non-fat dried milk; PAP, peroxidase anti-peroxidase; TBS, tris-buffered saline; and ug, microgram.

SUMMARY OF THE INVENTION

The present invention involves a method for separating biological molecules by subjection of said molecules to a separation system in a gel medium. The method most particularly involves the use of a gel slab suitable for such separations which is readily equilibrated with an appropriate solvent for the chosen separation system.

This equilibration, it should be emphasized, takes place without removal of polymer additive from the gel. An important aspect of the present invention involves the initial preparation of a gel slab comprising between about 0.5% and about 2.0% agarose and between about 0.1% and about 5.0% (more preferably between about 1% and about 3%) linear water-soluble and substantially nonionic polyacrylamide. Partially ionic and other hydrophilic polymers such as polyethylene glycol, copolymers of acrylamide and methacrylamide, vinyl pyrrolidone or vinyl acetate may be used in certain circumstances. A preferred gel slab of the present invention contains between about 1% and 3% agarose and about 3% linear and water-soluble polyacrylamide. This polyacrylamide is preferably substantially nonionic, particularly for electrophoretic separation. The gel slabs of the present invention are preferably between about 1 mm and 0.5 mm in thickness.

The linear, water-soluble and substantially nonionic polyacrylamide, as utilized in certain processes of the present invention has a preferred molecular weight between $10^2$ and $10^9$, more preferably between about $1 \times 10^4$ and $1 \times 10^7$ and most preferably between about $1 \times 10^5$ and $3 \times 10^6$. These LPA molecular weight ranges are estimates relative to sieving rates seen with passage of globular proteins of known molecular weights through gel columns of known porosities. Shorter LPAs are preferred chains because they have lower viscosity; they simplify casting of the gel; and they don't cause the gel to stick to GelBond during removal from the casting frame. A linear polyacrylamide in such molecular weight range and usable in the practice of the present invention, may be obtained by purchase and/or purification or made by polymerization of acrylamide, for example, at a temperature between about 60° C. and about 68° C. The LPA's of the present invention may also be made at either lower or higher temperatures by varying the concentrations of the catalysts. The linear, water-soluble, substantially nonionic polyacrylamide, in the processes of the present invention, may be, most preferably, added as a preformed polymer to the as yet ungelled agarose or may be formed by polymerizing acrylamide monomeric units of the polyacrylamide in an agarose solution prior to or simultaneous with the agarose gelling. Isoelectric focusing (IEF) is a preferred separation system for use with the rapidly equilibratable gels of the present invention. In one embodiment of the present method, the gel slab, after initial preparation, is aged at a temperature of about 4° for a period of at least about 1 hr. A preferable aging time is from 6-7 days to ultimately achieve optimal rehydration. The linear, water-soluble, substantially nonionic polyacrylamide has its nonionic character most typically defined by being substantially without free charged groups. By the term "substantially without", a lack of anionic or cationic interaction with biological molecules or the agarose so as to substantially alter electrophoretic behavior of the molecules in separating systems is meant. This also means that the LPA will not alter agarose conductivity.

Said aged gel slab is then dried to produce a gel precursor sheet. A preferred drying procedure is to subject the gel slab to a stream of warm air to maintain a gel surface temperature of about 45°-50° C., a 0.5 mm gel slab taking about 6-8 min to dry under these conditions. The dried gel precursor sheet, preferably maintained in a dried state for less than about 24 hr, is immersed for at least about 30 min, for example at about 20° C., in an aqueous separation solvent compatible with the separation system to be subsequently utilized. Aqueous separation solvents usable for gel rehydration include those comprising one or more of detergents (preferably nonionic), urea (up to about 10M), ampholytes and pH buffers, for example, again depending upon the particular separation system to be used for separation of the biological molecules. Usable separation systems include electrophoresis, immunodiffusion and isoelectric focusing, for example.

The immersion of the dried gel precursor sheet results in the formation of a rehydrated and equilibrated gel slab having at least about 75% of its original wet weight. The rehydrated gel slab also retains approximately its original porosity to biological molecules. The biological molecules are applied to a surface of the rehydrated gel slab, or placed in precut or freshly formed wells, for example. Next, the biological molecules on the rehydrated gel slab are subjected to forces of the separation system, such as an electrical field or diffusive force, and migrate through the gel accordingly. This migration results in the separation of said biological molecules from one another in manners well known to those skilled in the relevant arts.

In one application, the present invention involves a method for separating biological molecules by subjection of said molecules to an isoelectric focusing separation system in a gel medium. This method comprises the steps of: preparing a gel slab comprising between about 0.5% and about 2.0% agarose and between about 1.0% and about 3.0% linear, water-soluble, substantially nonionic polyacrylamide; drying said gel slab; rehydrating the dried gel slab to at least about 75% of its original wet weight in an aqueous separation solvent comprising urea and an ampholyte; applying the biological molecules to the gel slab; and subjecting the biological molecule-containing gel slab to an electrical field to focus said biological molecules according to their net electrical charge.

Another specific application of the present invention involves separating biological molecules by subjection of said molecules to an electrophoretic separation system in a gel medium. This method comprises the steps of: preparing a gel slab comprising between about 0.5% and about 2.0% agarose and between about 1.0% and about 3.0% linear, water-soluble, substantially nonionic polyacrylamide; drying said gel slab; rehydrating the dried gel slab to at least about 75% of its original wet weight in a buffered aqueous separation solvent; applying the biological molecules to the gel slab; and subjecting the biological molecule-containing gel slab to an electrical field to separate said biological molecules according to their net electrical charge.

In another variation, the present invention involves a method for determining immunological properties of biological molecules by subjection of said molecules and antibodies to migration in a gel medium. This method comprising the steps of: preparing a gel slab comprising between about 0.5% and about 2.0% agarose and between about 1.0% and about 3.0% linear, water-soluble, substantially nonionic polyacrylamide; drying said gel slab; rehydrating the dried gel slab to at least about 75% of its original wet weight in an aqueous separation solvent comprising a pH buffer; applying the biological molecules to the gel slab; and allowing the biological molecules and the antibodies to migrate whereby antibody-biological molecule complexes form characteristic precipitin bands.

In an important aspect, the present invention comprises a gel slab which is dryable and rehydratable in an aqueous separation solvent to at least about 75% of its original weight without substantial decrease in porosity, the gel slab comprising between about 0.5% and about 2.0% agarose and between about 1.0% and about 3.0% linear, water-soluble, substantially nonionic polyacrylamide.

BRIEF DESCRIPTION OF THE DRAWINGS

FIG. 3 shows a comparison of the pH gradient of a normal versus a rehydrated gel. A normal gel and a rehydrated gel containing preformed LPA were subjected to IEF, and 2×10 mm sections of each gel were removed and the pH of each fraction was measured as described herein. Normal gels (O—O) and rehydrated gel (O—0) are so indicated.

FIG. 4 shows quantitation of transfer rate of proteins from normal and rehydrated gels to nitrocellulose. $^{125}$I-labelled proteins were separated by IEF on normal gels or rehydrated gels containing preformed LPA, and then transferred to nitrocellulose. Identical areas of the gel and membrane were removed and counted. The three proteins transferred were: (A) human IgG ($M_r$146,000); (B) bovine thyroglobulin ($M_r$ 670,000); and (C) human IgM ($M_r$ 970,000). Transfer rates from normal (O—O) and rehydrated (O—O) gels are indicated. Each point represents the average of two separate experiments.

DESCRIPTION OF PREFERRED EMBODIMENTS

Figure 1:
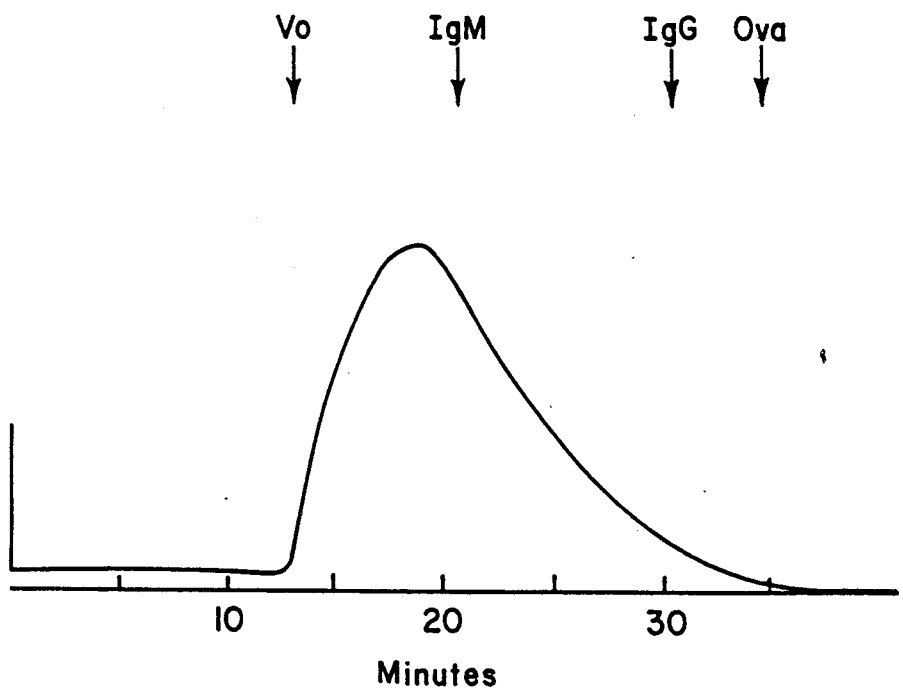
FIG. 1 shows the HPLC profile of a typical linear polyacrylamide preparation. Linear polyacrylamide was synthesized and processed as described herein, and the molecular weight was estimated on a Pharmacia Superose 6 column. The arrows at the top of the figure indicate the void volume ($V_o$) and the following molecular weights: IgM, (human) ($M_r$970,000); IgG, (human) ($M_r$146,000); and L Ova (ovalbumin) ($M_r$44,000).

The present invention involves methods for the preparation of rehydratable agarose gels containing a polymer such as linear nonionic polyacrylamide After drying the gels, rehydration and equilibration with an aqueous separation solvent takes about 30 minutes and occurs when an aqueous separation solvent is absorbed into the gel. The aqueous separation solvent may contain many different compounds, including denaturants such as urea at concentrations up to 10 M, non-ionic or ionic detergents such as Triton X-100 and temperature-sensitive reagents such as proteins, dyes, or other substances.

Proteins of at least 970,000 molecular weight, for example, may be separated by isoelectric focusing (IEF) in 30 min in the rehydrated gels with no greater pore size restriction than with the gel prior to drying and rehydration. The separated proteins may then be quanitatively transferred to nitrocellulose in less than 10 minutes, and any immunostaining or other staining or locating procedure may be used to probe the blotted proteins.

If linear polyacrylamide, for example, is added to any agarose stock before gel formation occurs, rehydratable gel can be cast in a variety of formats and used in other procedures such as immunoelectrophoresis and Ouchterlony immunodiffusion analysis.

Whether acrylamide monomers were polymerized in situ during the formation of the agarose gel or preformed LPA was added before the formation of the agarose gel, both the size and, most especially, the concentration of the polymers influenced the degree of rehydration and the pore size in the gel. In both types of rehydration gels, the pore size of the gel varied inversely with the percent of rehydration, and a higher LPA concentration decreased pore size. Increasing the chain length of the LPA, while keeping the percentage of LPA constant, resulted in a gradual decrease in pore size but a faster and better rehydration of the gel. The decrease in pore size in agarose gels caused by the addition of linear polymers has previously been shown to result in a molecular sieving effect that was directly related to the chain length and concentration of the different polymers tested (Bode (1977) Anal. Biochem. 83:204-210 and Horowitz et al. (1984) Anal. Biochem. 143:333-340). A major result of increased chain length is the ability to use less LPA. However, even at lower concentrations, the long chains may cause pore size reduction.

The chain length of the linear acrylamide polymers is dependent on the temperature of polymerization. Shorter polymers result when acrylamide is polymerized at higher temperatures (Andrews, A.T. (1986) Electrophoresis: Theory, Techniques and Biochemical and Clinical Applications, p.8, Oxford Press, Cambridge). Since shorter polymers are desirable in the preparation of rehydratable gels, this may explain why it was desirable to maintain the acrylamide-agarose solution at 63° C. for 3 min during the early stages of in situ polymerization of the acrylamide monomer. Rapid cooling of the polymerization solution resulted in a increase in the length of the LPA formed and a noticeable sieving of large protein aggregates during IEF. It was also preferred to heat the acrylamide solution to 63° C. during the formation of "preformed" LPA to obtain the preferred polymer length.

Although it was assumed that the chain lengths of the LPA in the in situ gels and the gels containing preformed LPA were similar, the preparation of the gels were different which resulted in rehydrated gels with different properties. Since the in situ gels were dialyzed and blotted before use in IEF, some LPA, especially shorter chains, was apparently removed from the gels. Because of this loss of LPA, 4.5% and not 2.25% acrylamide, was originally needed for polymerization. Although both gels probably contained 2.0-2.5% LPA during IEF, the longer LPA chains in the in situ gels apparently caused more molecular sieving of some protein aggregates.

Figures 2A, 2B, 2C:
FIG. 2 shows the resolution of protein standards on normal and rehydrated agarose gels. The resolving capability of a normal agarose gel (A) was compared with the resolving capability of rehydrated agarose gels containing either preformed LPA (B) or acrylamide monomers polymerized in situ (C). The following samples were put onto all three gels: lane 1, 40 ug horse ferritin; lane 2, 40 ug bovine thyroglobulin; lane 3, 40 ug monomeric human IgG; and lane 4, 10 ug human hemoglobin IEF and staining of the three gels was as described herein.

The two types of rehydration gels gave similar IEF patterns of four different protein monomers (FIG. 2B vs 2C). However, when compared with a normal gel (FIG. 2A), it was obvious that the Cohn fraction-II profile was less diffuse on the rehydratable gels. Since there were no major differences in the average mobility of proteins on the three different gels, and the pH gradients were very similar (FIG. 3), it was not known why this profile change occurred. Although Johansson (Johansson, B. G., and Hjerten, S. (1974) Anal. Biochem. 59:200-213) had previously shown that when linear polymers like methyl cellulose, polyethylene oxide or linear polyacrylamide were incorporated into an agarose gel there was a dramatic reduction in the endosmotic flow in the gels, this observation did not explain the profile change seen in FIG. 2.

Since 95% of the human IgG, human IgM and thyroglobulin was transferred to nitrocellulose from the rehydrated gels made with preformed LPA (FIG. 4), these gels may allow quantitative transfer to nitrocellulose of all proteins under 1,000,000 molecular weight. It was not known why the IgM molecules transferred to nitrocellulose at a higher efficiency from the rehydrated gel than from the normal gel, but this observation re-emphasized the fact that pore size was not noticeably decreased in the rehydratable agarose gels.

Figures 5A, 5B:
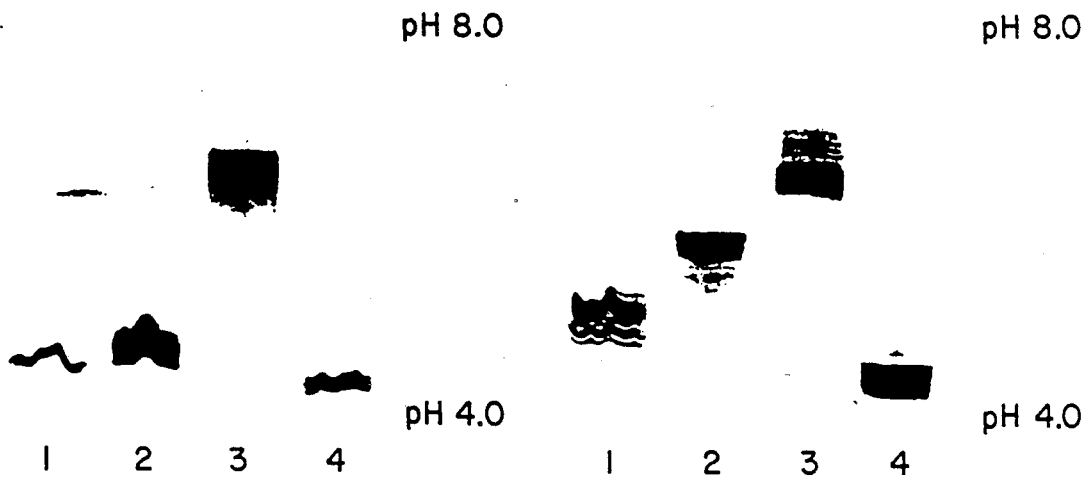
FIG. 5 shows stability of rehydrated agarose gels in 8 M urea. Gels containing LPA were rehydrated with a 3% ampholyte solution containing no urea (A) or 8M urea (B), and focused as described herein. The following samples were applied to each gel: lane 1, 40 ug ovalbumin; lane 2, 40 ug bovine serum albumin; lane 3, 40 ug human IgG myeloma-Bur.; and lane 4, 40 ug horse ferritin.

The rehydratable gels appeared to be very stable in 8M urea, but one of the tested proteins demonstrated a definite pH shift in its pI when electrophoresed in this denaturing solvent (FIG. 5). Since it was well known that urea decomposes to cyanate in a time and temperature dependent fashion ((Dirnhuber, P., and Schutz, F. (1948) Biochem. J., 42:628-632), and since it was also known that the cyanate modification of lysine residues (Stark, G. R., Stein, W. H., an Moore, S. (1960) J. Biol. Chem. 235:3177-3181) can change the pI of a protein, it might be assumed that the observed pI change was due to cyanate modification (see FIG. 5B). However, the rapid incorporation at 20° C. of fresh, ultra-pure urea into the IEF gels would argue against a high cyanate concentration in the gels. Also, since only the pI of BSA was modified, and the three other proteins did not show a significant change in their pI, cyanate was probably not responsible for the pI change of BSA in 8M urea. It is more likely that the 8M urea caused an unfolding of all proteins, and BSA had a dissociable group buried internally that now contributed to the pI of the molecule. In support of this argument, it has been reported that human serum albumin showed a similar shift in pI during IEF in 6 M urea (Ui, ! N. (1971) Biochim, Biophys, Acta 229:567-581), although three other proteins showed no pI change when analyzed under similar conditions.

In addition to decreased cyanate modification of proteins during usage of urea-containing buffers, another important advantage of the rehydratable agarose gels of the present invention is that, after protein aggregates are separated on gels containing, for example, 8 M urea, they can be efficiently transferred to nitrocellulose in an active form (FIG. 6). Since it has been demonstrated that 10 M urea can be easily incorporated into these gels, and that up to 95% of the protein can be transferred to nitrocellulose, this technique becomes a valuable tool in analyzing various other protein aggregates. These gels can be used in IEF and Ouchterlony immunodiffusion analysis, and any other procedure that uses agar or agarose as a support medium. Since dissociating agents like 10 M urea can be incorporated into these gels with no detectable deleterious effects, it is envisioned that a wide variety of aqueous solvents would be compatible with the rehydratable agarose gels. In addition, since transfer to nitrocellulose is rapid (10 min) and no trans-blotting equipment is needed for the passive diffusion, this technique may replace SDS electrophoresis in some situations. The only current limitations of the procedure may relate to gel thickness and gel storage. Since the percentage of gel rehydration tends to decrease as gel thickness increases, the use of 0.5 mm or thinner gels is encouraged. Also, since the agarose continues to slowly form new hydrogen bonds when it is dried, even in the presence of LPA, the dehydrated gels should be rehydrated on the same day they are dried and not stored in a dry form. The decrease in % rehydration during periods of dry storage was generally a few percent per week.

The following examples are presented to describe specific and preferred embodiments and utilities of the present invention and are not meant to limit the present invention unless otherwise specifically stated in the claims appended hereto.

MATERIALS AND METHODS

Reagents

Ovalbumin was obtained from Calbiochem, La Jolla, Ca. Bovine serum albumin was obtained from GIBCO, Grand Island, N.Y. Bovine thyroglobulin was obtained from Sigma Chemical Co., St. Louis, Mo. Blue Dextran 2000 was obtained from Pharmacia Fine Chemicals, Piscataway, N.J. Urea (Sequanal grade) was obtained from Pierce Chemical Co., Rockford, Ill. Acrylamide (electrophoresis grade) and TEMED were obtained from Bio-Rad Laboratories, Richmond, Calif. Rabbit peroxidase anti-peroxidase (PAP) complexes were obtained from Jackson ImmunoResearch Laboratories, West Grove, Pa.

Samples

A plasma sample containing a high titer of IgG rheumatoid factor from patient Lin was a generous gift from Dr. Richard Pope, University of Texas Health Science Center, San Antonio, Tex. Plasma IgG containing the IgG rheumatoid factor was purified by DE-52 chromatography (Smiley, J. D., Sachs, C., and Ziff, M. (1968) J. Clin. Invest. 47:624–632). An IgM monoclonal euglobulin was isolated from serum by precipitation in water. Monomeric human IgG was isolated by gel filtration chromatography of Cohn fraction-II on Bio-Gel A-5m (Bio-Rad Laboratories, Richmond, Calif.).

Iodination

Monomeric human IgG, thyroglobulin and the IgM monoclonal euglobulin were purified by gel filtration HPLC on a Superose 6 column (Pharmacia Fine Chemicals, Piscataway, N.J.), and then $^{125}$I-labelled using the lactoperoxidase method (David, G. S. (1972) Biochem. Biophys, Res. Commun. 48:464–471). Specific radioactivities varied between 1,000–2,000 cpm/ng, depending on the protein labeled.

Preparation of linear polyacrylamide

One liter of a freshly prepared 2% (w/v) stock of acrylamide was preheated on a stir plate to 63° C. While stirring at 63° C., 0.4 ml of N,N,N',N'-tetramethyethylenediamine (TEMED) and 4.0 ml of freshly prepared 10% (w/v) ammonium persulfate were rapidly added to polymerize the acrylamide monomers. Polymerization continued for 3.5 min at 63° C. until the solution was removed from the heat and the reaction was stopped by vigorously bubbling 95% oxygen through the solution for 5 min. After cooling, the linear polyacrylamide (LPA) was concentrated 10 fold by dialysis against 20% (w/v) polyethylene glycol (20,000 molecular weight). Following concentration, the dialysis bag containing the concentrated LPA was transferred to another beaker and repeatedly dialyzed against water until no free acrylamide monomers or TEMED could be detected in the dialyzate when reading at 220 nm and no small molecules could be detected on the HPLC profile. Usually 0.02% sodium azide was left out of the last two changes of buffer, since this compound absorbs at 220 nm and interferes with detecting other compounds in the dialysate. Concentrations of acrylamide and polyacrylamide were routinely determined by their light absorbancy at 220 nm. A 1% (w/v) stock of linear polyacrylamide read ·12.2 absorbance units at 220 nm as determined by gravimetric analysis. Purity and molecular size of the LPA were checked by HPLC on a Superose 6 column (Pharmacia Fine Chemicals, Piscataway, N.J.) and a typical profile is shown in FIG. 1. Flow rate was 0.5 ml/min, the buffer was 0.025 M phosphate (pH 6.8) containing 10% isopropyl alcohol (but no sodium azide), and the profile was analyzed at 220 nm. After purity and concentration were determined, 0.02% sodium azide was added to the LPA stock and the LPA was stored at 4° C.

Rehydratable agarose gels

Agarose gels that could be dried and rehydrated in a variety of aqueous solutions were prepared by two different methods, using either LPA formed in situ by polymerization of acrylamide monomers or preformed LPA.

When using acrylamide monomers, 100 mg of Pharmacia Agarose IEF (Lot No. ML 03211) was added to a flask containing 8.5 ml of distilled water. The flask was tightly covered with aluminum foil and heated (with stirring) in a beaker of boiling water for 5–10 min until the agarose was completely solubilized. After transferring the agarose solution to a 63° C. water bath, 2 ml of a freshly prepared solution of 30% acrylamide (monomers) were pre-heated in a covered tube for 5 min in the same 63° C. water bath. At the end of 5 min. 1.5 ml of the preheated acrylamide stock were added to the 8.5 ml of agarose solution and mixed on a stir plate in a beaker of water heated to about 63° C. The acrylamide in the mixture was polymerized by the addition of 4 ul TEMED and 40 ul of 10% ammonium persulfate (freshly prepared). After rapid addition of the catalysts, the mixture was stirred for 30 sec. and then rapidly transferred to a 10 ml syringe. The bubbles were then cleared from the barrel of the syringe and the 23 gauge needle, and the filled syringe was put back into the 63° C. water bath for 3 min. Usually, it took 75 sec to add the acrylamide and catalysts to the agarose solution, stir, and fill the syringe with the mixture. After waiting the 3 min, a pre-heated (63.C) casting assembly (95×95×0.5 mm) was rapidly filled with the agarose-polyacrylamide mixture as previously described (Hoffman, W. L., and Jump, A. A. (1985) J. Immunol. Methods 76:263–271). The gels solidified at room temperature in 15 min and were stored at least 1 hr at 4° C. before they were removed from the casting assembly. The gels were then covered with a second piece of GelBond and stored in a humidified chamber at 4° C.

It was easier to make rehydratable gels using the preformed LPA method, and there was less restriction of large proteins in these gels. The method of making the gels was as described above, but with the following changes. The 100 mg of agarose were solubilized in 7 ml of water and 3 ml of preformed LPA (7.5% w/v) were mixed and preheated at 63° C. Since all components were stable at 63° C., and there was no need for catalysts, rapid addition of reagents was not necessary. After adding 3 ml of the preheated LPA to the 7 ml of the solubilized agarose stock, filling the syringe with the mixture, and clearing the air bubbles from the syringe, the casting frames were filled as fast as possible. The resulting gel contained 2.25% LPA, although variations in the preparation of LPA could necessitate a slight adjustment of the LPA concentration to achieve a rehydration of at least 75%. Solidification of the gel and gel storage were as described above.

Gel dehydration

Gels were normally stored by covering the surface with an additional piece of GelBond and leaving the gel in a humidified box at 4° C. for 3-7 days to permit stabilization of the gel matrix before drying. If necessary, gels could be stored in the humidified box for at least six weeks, with no detectable change in rehydratability or IEF resolution. The method used to dry the gels may vary, but blowing warm air is preferred. The gels made with the pre-formed LPA were dried under the hot air of a blow dryer. The temperature on the gel surface was 45-50° C., and a 0.5 mm thick gel took about 6-8 min to dry completely. For optimal maintenance of porosity the gel should be rehydrated within about 24 hr of when it was dried.

The gels formed by the in situ polymerization of the acrylamide monomers (in situ gels) still contained acrylamide, acrylic acid and catalyst components in the gel that had to be removed. After storing the gels for at least 3 days at 4° C. as described above, the gels (95×95×0.5 mm) Were placed in a liter of distilled Water and stirred for 15 min. After stirring, a reusable piece of moistened nitrocellulose was put on each gel to prevent the filter paper from sticking to the gel surface, followed by a pre-wetted piece of #1 Whatman filter paper and six paper towels. The gel was then blotted on the paper towels for 5 min using a glass plate and a 0.5 kg weight (Hoffman, W. L., and Jump, A. A. (1985) J. Immunol. Methods 76:263-271). The blotting of the gel helped to speed the drying of the gel, and after blotting, the towels and filter paper were removed. To release the nitrocellulose membrane from the blotted gel, it was necessary to re-wet the nitrocellulose membrane before it was removed. The gels were then dried with the blow dryer as described above and used the same day.

Gel rehydration

Gels were routinely rehydrated in a casting frame (Methodology for Agarose Isoelectric Focusing, Immunofixation, and Related Techniques (1982) FMC Corporation, Rockland, Maine) immediately after they were dried under the blow dryer. However, it was advisable to wait at least 5 min after the gel was dried to allow the gel to uncurl before mounting it in the casting frame. Care was taken not to press too hard on the dehydrated gel with the gel roller and not to get water on the gel surface while the GelBond (with the dehydrated gel attached) was being attached to the wall of the casting frame. This meant that the roller had to be continually wiped off during the attachment of the GelBond to the glass surface. After the gel was attached to the wall of the casting frame and the frame was assembled with a 0.5 mm spacer inserted between the glass plates, rehydration began when the buffer of choice was added to the casting frame with a syringe. About 30 min at 20° C. was sufficient to rehydrate these gels to 75-80% of their original volume. After 30 min, the rehydrated gel was removed from the casting frame and was ready for use.

Percent rehydration

Gels varied in the degree of rehydration, depending on the amount of LPA incorporated into the gel. The percentage of original weight that the gel rehydrated was calculated as follows:

$$\text{percent rehydration} = \frac{(\text{rehydrated weight} - \text{dry weight}) \times 100\%}{(\text{original weight}) - (\text{dry weight})}$$

Agarose Isoelectric Focusing

Proteins were analyzed by IEF in agarose gels, as previously described ((Hoffman, W. L., and Jump, A. A. (1985) J. Immunol. Methods 76:263-271). Due to incompatibility between various lots of ampholytes and agarose, which resulted in the burning of all gels in the acidic region when buffer reservoirs were used instead of surface electrodes, both normal and rehydratable gels contained Pharmacia Agarose IEF (Lot No. ML 03211) and LKB Ampholine (1818-101, Batch #14). Regular IEF gels (95×95×0.5 mm) and rehydratable gels (95×95×0.6 mm) were run under similar conditions, but with the following changes. Since rehydrated gels were generally slightly thinner than normal gels, they were pre-blotted with one sheet of #1 Whatman filter paper for only 5-15 sec, instead of the normal 60 sec. This shorter pre-blot removed surface liquid from the gel, without making it too thin for the subsequent IEF analysis. After focusing rehydratable gels for 5 min at 6 w per gel, the constant power regulator was always adjusted to give 580 V to compensate for variations in gel thickness. In a regular gel, this normally equaled a constant power of 7 W, but in LPA rehydrated gels the 580 V resulted in a constant power of 4-6 W. Normal gels and in situ LPA gels were run for an additional 25 min, while pre-formed LPA rehydratable gels were normally run for an additional 20-22 min, before a final 5 min run at 2000 V. In the presence of urea, all gels were run at 4 W to prevent burning of the gel (Allen, R. C., Saravis, C. A., and Maurer, H. R. (1984) Gel Electrophoresis and Isoelectric Focusing of Proteins, p. 84, Walter de Gruyter, New York), and the total run time was extended to 35-45 min.

Acid fixing and staining of the agarose gels mounted on GelBond were as previously described (Hoffman, W. L., and Jump, A. A. (1985) J. Immunol. Methods 76:263-271).

pH gradients of agarose gels

After isoelectric focusing, slices of the agarose gel were removed from the gel at 1 cm intervals, starting 1 cm from the anode. These slices of the IEF gel (2×10 mm) were placed in 0.5 ml of distilled water and allowed to equilibrate in the water for 30 min. After equilibration, the pH of the water was read and the pH gradient of the gel was plotted.

Transfer of focused proteins to nitrocellulose

Transfer of proteins to nitrocellulose from both regular and rehydratable gels was as previously described (Hoffman, W. L., and Jump, A. A. (1985) J. Immunol. Methods LL 6 263-271), except that all gels were routinely rinsed for 15-20 s before blotting. This extended rinse time of the gel totally eliminated non-specific background. Only phosphate-buffered saline was used to soak the membrane and rinse the gel, since water will precipitate some IgM molecules in the gel. When transferring proteins to nitrocellulose from urea-containing gels, 6 M urea was included in the phosphate-buffered saline transfer medium.

Immunofixation and staining

After transfer of the IgG rheumatoid factor molecules to nitrocellulose, the unoccupied sites on the membrane were blocked with 5% non-fat dried milk (NFDM) in 20 mM Tris, 0.5 M NaCl, 0.01% thimerosal, pH 7.4 (TBS). After blocking for 1 hr, the membrane was then incubated for 1 hr at 20° C. in 5% NFDM-TBS, containing 20 ug/ml rabbit PAP. Following incubation with the PAP reagent, the membrane was washed for a total of 20 min in 0.5% NFDM-TBS, with two changes in that time period. After a final 5 min wash in TBS alone, the membrane was stained with 4-chloro-1-naphthol (Hoffman, W. L., and Jump, A. A. (1985) J. Immunol. Methods 76:263-271).

Quantitation of transfer rate

After transfer of the $^{125}$I-labelled proteins from the IEF gel to the nitrocellulose membrane, the areas containing the labelled proteins were located and cut out. Since the nitrocellulose membrane was not separated from the blotted gel until after the labelled proteins were cut out, identical areas were isolated. The membrane and gel fragments containing the $^{125}$I-labelled proteins were counted in a Packard Model 3002 gamma counter by carefully positioning the sample in the bottom of the tube to eliminate problems with counting geometry. Transfer rate was calculated by dividing the number of cpm transferred to the membrane by the total number of cpm in the gel and membrane fragments. All transfer studies were done in duplicate, and results were presented as an average of these data.

RESULTS

Many compounds incorporated into agarose gels at the time of gel formation did not permit the dried gels to rehydrate to at least 75% of their original weight. These compounds included polyvinylpyrrolidone ($M_r$40,000), polyethylene oxide ($M_r$900,000), methoxypolyethylene glycol ($M_r$5,000,000), and dextran ($M_r$2,000,000). Other compounds incorporated into agarose gels at the time of gel formation permitted the dried gels to rehydrate to >75% of their original weight, but they were not acceptable for use in IEF for two reasons. Either these compounds were ionic or were large enough to cause sieving of proteins in the gels. These compounds included 0.5% Blue Dextran 2000 ($M_r$2,000,000) and carboxymethylcellulose (1,500 centipoises at 2% w/v).

The nonionic compound that gave the best rehydration was linear polyacrylamide (LPA) ($M_r$>5,000,000) (British Drug House Chemicals). A gel containing 0.5% commercial LPA rehydrated rapidly to almost 100% of its original weight, but proved to be unacceptable because: (a) the high viscosity of the agarose-LPA solution made it difficult to cast gels; (b) the agarose gels routinely stuck to the hydrophobic side of GelBond; (c) large proteins were sieved by this gel; and (d) an ionic contaminant was present in the commercial LPA, and was not removed by either dialysis or purification by ion-exchange chromatography. This contaminant caused every gel to burn after 5 min of IEF.

When an LPA solution was prepared from electrophoretic grade acrylamide monomers and repeatedly dialyzed against distilled water, the resulting material did not have any of the problems associated with the commercial product. Polymerization was controlled to obtain a product of low viscosity and an apparent molecular weight of less than 3,000,000 (FIG. 1). When 2.25% of the new LPA was incorporated into agarose gels, the gels rehydrated to >75% of original weight and molecular sieving was not detected As the concentration of the LPA in the agarose gel was increased above 2.25%, the percent of rehydration increased but the apparent pore size of the gel decreased, as indicated by the sieving of large proteins. (It was assumed that the trailing and smearing of proteins on IEF gels were indications of molecular sieving, and that molecular sieving was directly related to pore size reduction Therefore, all comments about pore size herein were ascertained by visual examination of the degree of smearing on various gels.) As a result, between 2 and 2.5% LPA was routinely used because it permitted 75-80% rehydration of the gels with no detectable pore size reduction. It should be noted that non-rehydratable, IEF, agarose gels also typically weighed 75-80% of their original weight after pre-blotting one minute before sample addition (Hoffman, W. L., and Jump, A. A. (1985) J. Immunol. Methods 76:263-271).

When acrylamide monomers were added directly to the agarose solution and polymerization of the acrylamide was initiated before solidification of the agarose gel, the resulting agarose gel contained LPA formed by the in situ method. As with the preformed LPA gels, these in situ gels shared an inverse relationship between pore size and percent rehydration as the percent of linear polyacrylamide polymers was varied. However, the viscosity of the agarose solution during the casting of the in situ gel was substantially greater than in gels containing preformed LPA, since a higher percentage of acrylamide (4.5%) was needed in the in situ gels to compensate for the polymers lost during the subsequent dialysis At concentrations above 4.5% the in situ gels tended to stick to the hydrophobic surface of the GelBond in the casting frame and were more difficult to stain and destain than preformed LPA gels, because they tended to reswell in the staining solutions.

Care was exercised in the processing of both in situ and preformed LPA gels. Although dialysis of the in situ gels was needed to remove acrylic acid and catalysts from these gels before dehydration, an excess of either dialysis or blotting resulted in gels that did not rehydrate to at least 75% of their original weight. In contrast, the gels made with preformed LPA were not dialyzed because the LPA was already purified, and they were not blotted because if any of the 2.25% of the LPA was removed from the gels, the gels would not rehydrate properly. Both in situ and preformed LPA gels were routinely dried under a stream of forced hot air, since overnight drying of gels at 20° C. caused a permanent curling of the GelBond, and this made it difficult to put the gels into casting frames for rehydration.

FIG. 2 compares the resolution of a normal (non-rehydratable) gel (FIG. 2A) with rehydratable agarose gels formed either by the incorporation of preformed LPA (FIG. 2B) or by the in situ polymerization of acrylamide monomers (FIG. 2C). All proteins were resolved on the three gels, and the protein patterns on the rehydrated gels were very similar to one another. However, the rehydratable gels, compared to the normal gel, tended to give a more compressed pattern of the Cohn fraction-II sample, even though the pH gradient in both types of gels appeared to be similar (FIG. 3).

FIG. 4 shows that both human IgG and thyroglobulin were quantitatively transferred to nitrocellulose from both regular and preformed LPA rehydrated gels. Human IgM ($M_r$ 970,000) also transferred well to nitrocellulose from the rehydrated gel, and it should be noted that the transfer of IgM to nitrocellulose was better in the rehydrated gel than the normal gel. In subsequent studies comparing the preformed LPA versus in situ LPA rehydratable gels, 73% of the labeled IgM transferred to nitrocellulose from the in situ gel in 20 min, while 95% of the same protein transferred from the preformed LPA rehydratable gels under the identical transfer conditions. The slower transfer rate from the in situ LPA gels suggested that they have smaller pores than the preformed LPA gels. This idea was strengthened by the observation that IgG aggregated and precipitated near the sample application site on the in situ LPA gels, but entered the gels made with preformed LPA.

Since the rehydratable gels were very similar to normal gels in the separation of proteins by IEF and transfer of proteins to nitrocellulose, it was important to ascertain what range of compounds could be incorporated into these gels. It was found that the dried gels absorbed all the aqueous solutions tested, although higher ionic strength buffers sometimes did not rehydrate the gels as well as lower ionic strength buffers. When 5% Triton X-100 was incorporated at room temperature, there was no problem with the detergent falling out of solution at its cloud point (63° C.), which was a problem when the detergent was added during the casting of a normal gel.

FIG. 5 demonstrates the stability of the rehydrated gels in 8 M urea, and shows that satisfactory resolution of proteins was obtained Only the bovine serum albumin had a significant change in pI in 8 M urea (compare lane 2 in panels A and B). Gels containing 9 M urea were also routinely used in IEF and the protein patterns were similar to those obtained on 8 M urea gels. Although 10 M urea could be absorbed into the rehydratable agarose gels with no apparent damage to the gel structure, it was not routinely used because it tended to crystallize rapidly on the cooling platform during IEF.

Figures 6A, 6B:
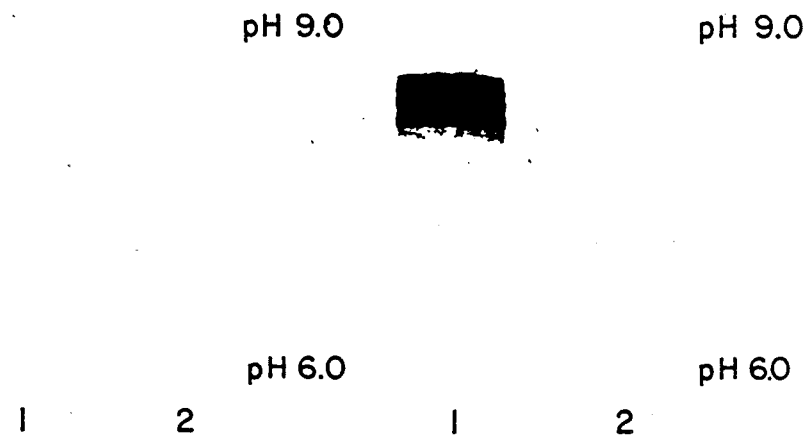
FIG. 6 shows dissociation of protein complexes in rehydrated agarose gels containing 8 M urea. Gels containing LPA were rehydrated with a 3% ampholyte solution containing no urea (A) or 8 M urea (B), and focused as described herein. The following samples were applied to each gel: lane 1, 500 ng of IgG rheumatoid factor (Lin); and lane 2, 400 ng of monomeric human IgG. After transfer to a nitrocellulose membrane, dissociated IgG rheumatoid factor complexes were detected by the binding of a rabbit PAP complex, as described in Methods

An important advantage of being able to incorporate high concentrations of urea into an IEF gel is that protein complexes can be dissociated during IEF and these proteins can then be transferred to nitrocellulose in an active conformation (Hoffman, W. L., and Jump, A. A. (1985) J. Immunol. Methods 76:263-271). For example, human IgG rheumatoid factor complexes normally exist in a complexed state with other rheumatoid factors, and will only bind to the Fc portion of IgG (human or rabbit) when the rheumatoid factor complex is dissociated. The human IgG rheumatoid factor-Lin did not bind the rabbit PAP complex in the absence of urea (FIG. 6A, lane 1) but did bind the rabbit PAP complex after IEF in a gel containing 8 M urea (FIG. 6B, lane 1). Therefore, not only did the 8 M urea dissociate the IgG rheumatoid factor complex, but the dissociated proteins retained their biological activity after transfer to the nitrocellulose membrane. Non-rheumatoid factor human IgG did not bind the rabbit PAP complex either in the presence or absence of 8 M urea (FIG. 6A and 6B, lane 2).

When phosphate buffered saline was absorbed into a rehydratable gel for Ouchterlony immunodiffusion analysis and the titer of rabbit anti-BSA was determined with BSA as the standard, the resulting pattern was identical to that obtained on a normal gel that was not rehydrated. This experiment and others, using agarose and agar from various suppliers, demonstrated that rehydratable agarose gels can be used in a wide variety of applications. However, during these studies, it was noted that gel thickness influenced the rehydratability of the gels. Gels thicker than 0.5 mm did not rehydrate as well as 0.5 mm gels on a percentage basis. For example, 0.5 mm gels rehydrated to 75-85% of their starting weight, while 1.5 mm gels rehydrated to only 50-55% of their original weight in the standard 30-45 min rehydration period. Longer rehydration times may increase the rehydratability of thicker gels, but this has not been investigated.

STUDY ON VARIATIONS IN THE PREFERRED PROCEDURES OF THE PRESENT INVENTION

Linear polyacrylamide (LPA) was prepared according to the directions in example 4 of U.S. Pat. No. 4,048,377. A 5% solution of this LPA was extremely viscous as compared to LPA prepared as described in Example 1 above. A 3% solution of the LPA from U.S. Pat. No. 4,048,377 was too viscous to pass through a 25 gauge or 18 gauge needle utilized in the preparation of a gel slab. Hence a gel comprising agarose and 3% U.S. Pat. No. 4,048,377 LPA was free cast and then the casting frame clamped together. This gel slab, after drying was rehydratable to more than 75% of its original gel volume. Upon use of this gel for separation of proteins by isoelectric focusing, it was noted that the rehydrated gel was usable but noticeably sieved proteins having molecular weight greater than 400,000, in contrast to gels prepared with LPA produced according to the methods of the present invention as described above. It did, however, appear that the gel slab prepared with LPA from U.S. Pat. No. 4,048,377 re-swelled during staining. This apparent ability for repeated rehydrations perhaps characteristic of such large LPA may provide advantages for future applications. It was additionally noted that agarose gel slabs comprising 2% LPA from U.S. Pat. No. 4,048,377 also exhibited definite sieving of globular proteins having molecular weights over about 600,000. It was noted that gels prepared according to example 4 of U.S. Pat. No. 4,048,377 were difficult to deal with since they repeatedly stuck to the casting frame and were usually damaged during removal. A preparation of LPA polymers having about 15% of the length of the polymers described in example 1 were prepared These shorter LPA polymers were incorporated into agarose gels and the properties of the gels studied. It was observed that these gels had about the same rehydration capabilities and porosity as gels prepared with LPA 5-6 times as large. It was noted that both rehydration and sieving were related to the concentration of LPA in the agarose rather than the LPA length. In one experiment it was noted that the acrylamide monomer itself permitted 60% rehydration for a gel slab. It thus appears that at least a degree of polymerization of the acrylamide is preferred. This polymerization optimizes the degree of rehydration and also facilitates minimal changes by loss of small molecular weight materials during rehydration and in preparation for use in separation of proteins. In one experiment it was noted that gel slabs prepared with 0.7% LPA from 4,048,377 were able to rehydrate to about 66% of their original volume and said rehydrated gels were usable in isoelectric focusing.

The following Table summarizes additional information on other non-ionic compounds tested for their ability to permit rehydration of agarose gels. The agarose gels were about 1% agarose and were processed and measured as described above.

| COMPOUND | % REHYDRATION | EXC SI |
|---|---|---|
| 2.0% dextran (MW 2,000,000) | 31% | |
| 0.5% methoxypolyethylene glycol (MW 5,000,000) | 18% | |
| 0.5% methylcellulose (visosity = 4000 cp) | 68% | |
| 1.0% polyethylene oxide (MW 900,000) | 60% | |
| 1.0% polyvinylpyrrolidone (MW 40,000) | 21% | |
| 0.5% linear polyacrylamide (MW > 5,000,000) | 95% | |

In situ polymerization was used to prepare 1% agarose gels containing the polymers described in the following Table and rehydration capacity of dried gels was measured as previously described.

| In Situ Polymerization Using: | % Rehydration |
|---|---|
| 100% acrolein | 0% |
| 50% acrylamide:50% vinyl acetate | 73% (cloudy) |
| 50% acrylamide:50% 1-vinyl-2-pyrrolidinone | >90% |
| 100% methacrylamide:0% acrylamide | 57% |
| 75% methacrylamide:25% acrylamide | 52% |
| 50% methacrylamide:50% acrylamide | 63% |
| 25% methacrylamide:75% acrylamide | >90% |
| 0% methacrylamide:100% acrylamide | >95% |

Preliminary results using polyethylene glycol (PEG) in rehydratable agarose gels were very encouraging. However, after extensive studies, it appears that PEG should not replace linear polyacrylamide (LPA) as the standard rehydrating agent for at least some applications.

Like LPA, PEG should be used at a concentration of 2.25–2.50%, and for many applications involving lower molecular weight molecules, PEG would be excellent. PEG ($M_r$ 8,000) shows gel rehydration to 100% of original weight and may actually be a better rehydrating agent than LPA. However, the PEG gels were not compatible with 9M urea which limits application of such gels.

The following table lists additional polymers useful or potentially useful in the preparation and uses of its rehydratable agarose gels of the present invention and properties of 1% agarose gels containing various amounts of these polymers.

| Polymer (MW) | Conc. | Cure Time | Rehydration (30 min) |
|---|---|---|---|
| Amylopectin | 2.5% | 19 hr | 43% |
| Dextran (2,000,000) | 2.5% | 20 hr | 51% |
| Linear polyacrylamide (1,000,000) | 2.5% | 20 hr | 75% |
| | 2.5% | 10 days | 92% |
| Methoxypolyethylene glycol (5,000) | 2.5% | 19 hr | 84% |
| | 2.5% | 10 days | 90% |
| Methylcellulose (400 c.p.) | 0.5% | 20 hr | 26% |
| Methylcellulose (1,500 c.p.) | 0.5% | 20 hr | 52% |
| Polyethylene glycol (3,350) | 2.5% | 4 days | 72% |
| Polyethylene glycol (8,000) | 2.5% | 4 days | 89% |
| | 2.5% | 7 days | 100% |
| Polyethylene glycol (20,000) | 2.5% | 4 days | 78% |
| Poly(ethylene oxide) (100,000) | 2.5% | 19 hr | 37% |
| Poly(ethylene oxide) (900,000) | 2.5% | 19 hr | No gel |
| | 2.5% | 13 days | 55% |
| Polyvinylpyrroidone (40,000) | 2.5% | 19 hr | 42% |
| Polyvinylpyrroidone (360,000) | 2.5% | 19 hr | 72% |
| Carboxymethyl cellulose (med. visoc.)* | 0.5% | 1 hr | 106% |
| Carboxymethyl cellulose (high visoc.)* | 0.5% | 1 hr | 106% |
| Blue Dextran 2, (2,,000)* | 1.0% | 1 hr | >90% |

*Highly charged polymers, which can be used in some applications, but not IEF.

It generally appears that oxygen, nitrogen or fluorine groups in the rehydrating compound are needed to hydrogen-bond to the agarose molecules to permit rehydration in agarose gels.

It should be noted from the prior table that an adequate cure time is needed for maximum rehydration of the agarose gels. After an adequate cure time, the maximum rehydration rate of LPA gels was maintained for at least six months. Copolymers could also be made ahead of time and then added to the agarose solution during casting of the gel.

Changes may be made in the composition, construction, operation and arrangement of the various elements, steps and procedures described herein without departing from the concept and scope of the invention as defined in the following claims.

What is claimed is:

1. A method for separating biological molecules by subjection of said molecules to a separation system in a gel medium, the method comprising the steps of:
    preparing a first gel slab consisting essentially of between about 0.5% and about 2.0% agarose and between about 0.1% and about 5% water-soluble substantially nonionic synthetic linear polymer;
    drying said slab to produce a dried gel precursor sheet;
    immersing the dried gel precursor sheet for at least 30 min in an aqueous separation solvent compatible with a separation system to be utilized to form a rehydrated and equilibrated gel slab having at least about 75% of its original wet weight, wherein said rehydrated gel as a porosity about equal to that of the first gel slab;
    applying a biological sample comprising macromolecules to the rehydrated gel slab; and
    subjecting the biological sample comprising macromolecules in the rehydrated gel slab to forces of the separation system to separate said macromolecules.

2. The method of claim 1 wherein the synthetic polymer is polyacrylamide, polyethylene glycol, acrylamide:vinyl acetate copolymer, acrylamide:1-vinyl-2-pyrrolidone copolymer, acrylamide: methacrylamide copolymer, polyethylene oxide, methoxypolyethylene glycol or methylcellulose.

3. The method of claim 1 wherein the immersing step is for about 30 min and results in an equilibrated and at least 65% rehydrated gel slab ready for separative uses.

4. The method of claim 1 wherein the water-soluble synthetic polymer is at a concentration between about 1.0% and about 3.0%.

5. A method for separating a biological molecules by subjection of said molecules to a separation system in a gel medium, the method comprising the steps:
preparing a first gel slab consisting essentially of between about 0.5% and about 2.0% agarose and between 1.0% and 3.0% linear, water-soluble, substantially nonionic polyacrylamide;
drying said gel slab to produce a gel precursor sheet;
immersing the dried gel precursor sheet for at least about 30 min in an aqueous separation solvent compatible with a separation system to be utilized to form a rehydrated gel slab having a porosity about equal to that of the first gel slab, and equilibrated with the separation solvent, wherein said equilibration takes place without removal of the polymer;
applying biological molecules to the rehydrated gel slab; and
subjecting the biological molecules on the rehydrated gel slab to forces of the separation system to separate said biological molecules.

6. A method for separating biological molecules by subjection of said molecules to a separation system in a gel medium, the method comprising the steps of:
preparing a first gel slab consisting essentially of between about 0.5% and about 2.0% agarose and between 1.0% and 3.0% linear, water-soluble, substantially nonionic polyacrylamide;
drying said first gel slab to produce a gel precursor sheet and maintaining the dried gel precursor sheet in a dried state for less than about 24 hrs;
immersing the dried gel precursor sheet in an aqueous separation solvent compatible with the separation system to be utilized to form a rehydrated gel slab having at least about 75% of its original wet weight and a porosity of about equal to that of the first gel slab before drying;
applying biological molecules to the rehydrated gel slab; and
subjecting the biological molecules on the rehydrated gel slab to forces of the separation system to separate said biological molecules.

7. The method of claim 1, 5 or 6 wherein the separation system is defined further as comprising isoelectric focusing.

8. The method of claim 1, 5 or 6 wherein the separation system is defined further as comprising immunodiffusion.

9. The method of claim 1, 5 or 6 wherein the separation system is defined further as comprising electrophoresis.

10. The method of claim 1, 5 or 6 wherein the immersing step is defined further as being at a temperature of about 20° C.

11. The method of claim 1, 5 or 6 wherein the aqueous separation solvent is defined further as comprising a detergent.

12. The method of claim 1, 5 or 6 wherein the aqueous separation solvent comprises a nonionic detergent and the separation system is isoelectric focusing.

13. The method for separating biological molecules by subjection of said molecules to a separation system in a gel medium, the method comprising the steps of:
preparing a first gel slab consisting essentially of between about 0.5% and about 2.0% agarose and between 1.0% and 3.0% linear, water-soluble, substantially nonionic preformed linear polyacrylamide;
drying said gel slab to produce a dried gel precursor sheet;
immersing the dried gel precursor sheet in an aqueous separation solvent compatible with the separation system to be utilized to form a rehydrated gel slab having at least about 75% of its original wet weight and having a porosity about equal to that of the first gel slab;
applying biological molecules to the rehydrated gel slab; and
subjecting the biological molecules on the rehydrated gel slab to forces of the separation system to separate said biological molecules.

14. The method of claim 1, 5 or 13 wherein the aqueous separation solvent comprises an ampholyte suitable for use in isoelectric focusing.

15. The method of claim 1, 5 or 13 wherein the aqueous separation solvent is defined further as comprising a nonionic detergent.

16. A method for producing an agarose-comprising gel slab equilibrated with an aqueous separation solvent and suitable for the application and separation of biological molecules, the method comprising:
preparing a gel slab by gelation of a solution comprising between about 0.5% and about 2.0% agarose and between about 0.1% and about 3.0% linear, water-soluble, substantially nonionic polyacrylamide;
aging the gel slab at about 4° C. for a period of at least about 1 hr;
drying said gel slab by directing a flow of warm air thereupon and maintaining the slab in a dried state for less than about 24 hr; and
rehydrating the dried gel slab in an aqueous separation solvent so that the gel slab recovers at least about 75% of its original wet weight.

17. A method for producing an agarose-comprising gel slab equilibrated with an aqueous separation solvent and suitable for the application and separation of biological molecules, the method comprising:
preparing a gel slab by gelation of a solution comprising between about 0.5% and about 2.0% agarose and between about 1.0% and about 3.0% linear, water-soluble, substantially nonionic polyacrylamide;
aging the gel slab at about 4° C. for a period of at from 6 to 7 days;
drying said gel slab by directing a flow of warm air thereupon and maintaining the slab in a dried state for less than about 24 hr; and
rehydrating the dried gel slab in an aqueous separation solvent so that the gel slab recovers at least about 75% of its original wet weight.

18. The method of claim 5 or 16 wherein the gel slab comprises about 1% agarose and between about 2% and about 3% linear, water-soluble, substantially nonionic polyacrylamide.

19. The method of claim 5 or 16 wherein the linear, water soluble polyacrylamide is defined further as having a molecular weight between about $1 \times 10^5$ and about $3 \times 10^6$.

20. The method of claim 5 or 16 wherein the preparing step is defined further as comprising adding a preformed linear, water-soluble, substantially nonionic polyacrylamide to an agarose solution prior to gelling of said solution.

21. The method of claim 20, wherein the substantially nonionic polyacrylamide is produced by polymerization of acrylamide at a temperature between about 60° C. and about 68° C.

22. The method of claim 5 or 16 wherein the preparing step is defined further as comprising polymerizing monomeric units of the linear, water-soluble, substantially nonionic polyacrylamide in an agarose solution prior to the gelling of said solution 23. The method of claim 5 or 16 wherein the linear, water-soluble, substantially nonionic polyacrylamide is defined further as being substantially without free cationic or anionic groups.

24. The method of claim 5 or 16 wherein the linear, water-soluble, substantially nonionic polyacrylamide is defined further as being substantially without free carboxyl groups.

25. The method of claim 5 or 16 wherein the linear, water-soluble, substantially nonionic polyacrylamide is defined further having a molecular weight of between about $10^2$ and $10^9$.

26. The method of claim 25 wherein the linear, water-soluble, substantially nonionic polyacrylamide is defined further as having a molecular weight of between about $10^1$ and $10^7$.

27. The method of claim 16 wherein the rehydrated gel slab is defined further as having a porosity substantially equal to that of the gel slab prior to drying.

28. The method of claim 27 wherein the gel slab has a surface and the stream of warm air maintains a gel surface temperature of about 45° C–50° C.

29. The method of claim 1, 5 or 16 wherein the gel slab has a thickness of less than about 1 mm.

30. The method of claim 1, 5 or 16 wherein the gel slab has a thickness of about 0.5 mm.

31. The method of claim 1, 5 or 16 wherein the aqueous separation solvent comprises urea.

32. The method of claim 1, 5 or 16 wherein the aqueous separation solvent is defined further as comprising urea at a concentration of at least 4 M.

33. The method of claim 1, 5 or 16 wherein the aqueous separation solvent is defined further as comprising 10 M urea.

34. A method for separating biological molecules by subjection of said molecules to an isoelectric focusing separation system in a gel medium, the method comprising the steps of:
preparing a gel slab consisting essentially of between about 0.5% and about 2.0% agarose and between about 1.0% and about 3.0% linear, water-soluble, substantially nonionic polyacrylamide;
drying said gel slab;
rehydrating the dried gel slab to at least about 75% of its original wet weight in an agarose separation solvent comprising urea and an ampholyte, wherein said rehydrated gel has a porosity about equal to that of the gel slab before drying;
applying the biological molecules to the gel slab; and
subjecting the biological molecule-containing gel slab to an electrical field to separate said biological molecules according to their net electrical charge.

35. A method for separating biological molecules having a molecular weight as great as 970,000 by subjection of said molecules to an electrophoretic separation system in a composite agarose polyacrylamide gel medium, the method comprising the steps of:
preparing a first gel slab consisting essentially of between about 0.5% and about 2.0% agarose and between about 1.0% and about 3.0% linear, water-soluble, substantially nonionic polyacrylamide;
drying said gel slab;
rehydrating the dried gel slab to at least about 75% of its original wet weight in a buffered aqueous separation solvent to provide a rehydrated composite gel containing the linear polyacrylamide and having a porosity about equal to that of the first gel slab;
applying the biological molecules of as great as 970,000 molecular weight to the rehydrated gel slab; and
subjecting the biological molecule-containing gel slab to an electrical field to separate said biological molecules according to their net electrical charge.

36. A gel slab which is dryable and rehydratable in an aqueous separation solvent to at least about 75% of its original wight without substantial decrease in porosity, the gel slab consisting essentially of between about 0.5% and about 2.0% agarose and between about 1.0% and about 3.0% linear, water-soluble, substantially nonionic polyacrylamide.

* * * * *

UNITED STATES PATENT AND TRADEMARK OFFICE
CERTIFICATE OF CORRECTION

PATENT NO. : 4,999,340

DATED : March 12, 1991

INVENTOR(S) : Wayne L. Hoffman, et al

It is certified that error appears in the above-identified patent and that said Letters Patent is hereby corrected as shown below:

Column 18, line 56 between the words 'gel' and 'a' delete the word "as" and insert the word --has-- therefor.

Column 21, line 29 delete the term "$10^1$" and insert the term --$10^4$-- therefor.

Column 22, line 43 delete the word "wight" and insert the word --weight-- therefor.

Signed and Sealed this

Eighteenth Day of August, 1992

Attest:

DOUGLAS B. COMER

*Attesting Officer*  *Acting Commissioner of Patents and Trademarks*

UNITED STATES PATENT AND TRADEMARK OFFICE
CERTIFICATE OF CORRECTION

PATENT NO. : 4,999,340

DATED : March 12, 1991

INVENTOR(S) : Wayne L. Hoffman; Adrien A. Jump,

It is certified that error appears in the above-identified patent and that said Letters Patent is hereby corrected as shown below:

On Title page;

On page 2, first column, line 14 delete the word "Effective" and insert the term --Effect of-- therefor.

On page 2, first column, line 17 delete the word "Silmey" and insert the word --Smiley-- therefor.

On page 2, first column, line 20 delete the word "Lactoperoxidiase" and insert the word --Lactoperoxidase-- therefor.

On page 2, second column, line 21 delete the large space between the word 'Agarose' and the word 'Gels'.

Column 1, line 5 delete the word "The" and insert the phrase --The present invention involves the preparation and-- therefor.

Column 1, line 61 delete the term "((" and insert --(-- therefor.

Column 2, line 51 delete the word "Rann" and insert --Renn-- therefor.

Column 2, line 65 delete the word "Ureal" and insert --Uriel-- therefor.

UNITED STATES PATENT AND TRADEMARK OFFICE
CERTIFICATE OF CORRECTION

PATENT NO. : 4,999,340

DATED : March 12, 1991

INVENTOR(S) : Wayne L. Hoffman; Adrien A. Jump,

It is certified that error appears in the above-identified patent and that said Letters Patent is hereby corrected as shown below:

Column 3, line 23-24 delete the phrase "Andrews (page 148-153, 1986) ELECTROPHORESIS, Oxford Press)" and insert the phrase --(Andrews, A.T. (1986) Electrophoresis: Theory, Techniques and Biochemical and Clinical Applications, Page 148-153, Oxford Press, Cambridge)-- therefor.

Column 3, line 40 delete the word "endoosmotic" and insert --endosmotic-- therefor.

Column 6, line 10 delete the term "L".

Column 6, line 20 insert the mark --.-- after the phrase 'globin'.

Column 6, line 27 delete "o—o" and insert -- •—• -- therefor.

Column 6, line 37 delete"o—o" and insert -- •—• -- therefor.

Column 7, line 11 delete the word "quanitatively" and insert --quantitatively-- therefor.

Column 7, line 53 delete the word "a" and insert the word --an-- therefor.

Column 8, line 35 delete the term "((" and insert --(-- therefor.

Column 8, line 53 delete the "!".

UNITED STATES PATENT AND TRADEMARK OFFICE
CERTIFICATE OF CORRECTION

PATENT NO. : 4,999,340

DATED : March 12, 1991

INVENTOR(S) : Wayne L. Hoffman; Adrien A. Jump,

It is certified that error appears in the above-identified patent and that said Letters Patent is hereby corrected as shown below:

Column 8, line 53 delete the mark "," after 'Biochim' and insert a -- . -- therefor.

Column 8, line 54 delete the mark "," after 'Biophys' and insert a -- . -- therefor.

Column 9, line 61 delete the large space at the beginning of the line.

Column 9, line 61 delete the mark "," after 'Biophys' and insert a -- . -- therefor.

Column 9, line 68 to Column 10, line 1, delete the word "tetramethyethyllenediamine" and insert the word --tetramethylethylenediamine-- therefor.

Column 10, line 64 delete "63.C" and insert --63°C.-- therefor.

Column 11, line 44 delete the word "Were" and insert --were-- therefor.

Column 11, line 44 delete the word "Water" and insert --water-- therefor.

Column 12, line 29 delete the term "((" and insert --(-- therefor.

Column 12, line 38 delete "0.6 mm" and insert --0.5 mm-- therefor.

UNITED STATES PATENT AND TRADEMARK OFFICE
CERTIFICATE OF CORRECTION

PATENT NO. : 4,999,340

DATED : March 12, 1991

INVENTOR(S) : Wayne L. Hoffman; Adrien A. Jump,

It is certified that error appears in the above-identified patent and that said Letters Patent is hereby corrected as shown below:

Column 12, line 46 delete the "w" and insert --W-- therefor.

Column 13, line 10 delete the phrase "Methods LL 6 263-271" and insert --Methods 76:263-271-- therefor.

Column 13, line 24 delete the terms "NaCI" and insert the term --NaCl-- therefor.

Column 14, line 21 insert a --.-- after the word 'detected'.

Column 14, line 28 insert a --.-- after the word 'reduction'.

Column 14, line 52 insert a --.-- after the word 'dialysis'.

Column 15, line 50 insert a --.-- after the word 'obtained'.

Column 16, line 46-line 47 delete divided word "prote - ins" and insert --pro - teins-- therefor.

Column 16, line 53 insert a --,-- after the word 'rehydrations'.

Column 16, line 54 insert a --,-- after the term 'LPA'.

Column 16, line 64 insert a --.-- after the word 'prepared'.

Column 17, line 12 insert the term --U.S. Pat. No.-- after the word 'from' therefor.

Column 17, line 23 delete the term "EXC/SI".

UNITED STATES PATENT AND TRADEMARK OFFICE
CERTIFICATE OF CORRECTION

PATENT NO. : 4,999,340

DATED : March 12, 1991

INVENTOR(S) : Wayne L. Hoffman; Adrien A. Jump,

It is certified that error appears in the above-identified patent and that said Letters Patent is hereby corrected as shown below:

Column 18, line 2-line 3 change the table heading to:
--Cure      Rehydration--
--Conc.    Time       (30 min)--

Column 18, line 17 delete the word "Polyvinylpyrroidone" and insert the word --Polyvinylpyrrolidone-- therefor.

Column 18, line 18 delete the word "Polyvinylpyrroidone" and insert the word --Polyvinylpyrrolidone-- therefor.

Column 18, line 23 delete the phrase "2, (2,,000)" and insert the phrase --2,000 (2,000,000)-- therefor.

In claim 5, column 19, line 7 delete the word "a" between the words 'separating' and 'biological'.

UNITED STATES PATENT AND TRADEMARK OFFICE
CERTIFICATE OF CORRECTION

PATENT NO. : 4,999,340

DATED : March 12, 1991

INVENTOR(S) : Wayne L. Hoffman; Adrien A. Jump

It is certified that error appears in the above-identified patent and that said Letters Patent is hereby corrected as shown below:

In claim 5, column 19, line 9 delete the phrase "steps:" and insert the phrase --steps of:-- therefor.

In claim 16, column 20, line 31 delete the term "0.1%" and insert the term --1.0%-- therefor.

In claim 16, column 20, line 51 delete the word "at" after the word 'of'.

In claim 22, column 21, line 13 insert a --.-- after the word 'solution'.

In claim 25, column 21, line 24 insert the word --as-- after the word 'further'.

Signed and Sealed this

Twenty-second Day of December, 1992

*Attest:*

DOUGLAS B. COMER

*Attesting Officer*     Acting Commissioner of Patents and Trademarks